United States Patent [19]
Wong et al.

[11] Patent Number: 5,814,304
[45] Date of Patent: Sep. 29, 1998

[54] STABLE AQUEOUS ABRASIVE PEROXIDE TOOTH WHITENING DENTIFRICE

[75] Inventors: Michael Wong, North Brunswick; Michael Prencipe, West Windsor; Kedar N. Rustogi, Kendall Park, all of N.J.

[73] Assignee: Colgate Palmolive Company, New York, N.Y.

[21] Appl. No.: 891,010

[22] Filed: Jul. 10, 1997

Related U.S. Application Data

[63] Continuation-in-part of Ser. No. 692,841, Aug. 2, 1996.

[51] Int. Cl.$^6$ .............................. A61K 7/16; A61K 7/20; A61K 33/40
[52] U.S. Cl. ............................... 424/53; 424/49; 424/63; 424/616
[58] Field of Search ................................. 424/49–58

[56] References Cited

U.S. PATENT DOCUMENTS

| | | | |
|---|---|---|---|
| 1,958,204 | 5/1934 | Reichert | 23/251 |
| 2,027,838 | 1/1936 | Reichert | 23/251 |
| 2,904,517 | 9/1959 | Baker | 252/397 |
| 3,114,606 | 12/1963 | Meeker | 23/207.5 |
| 3,333,925 | 8/1967 | Young | 23/207.5 |
| 3,607,053 | 9/1971 | Reilly | 23/207.5 |
| 3,811,833 | 5/1974 | Stalter | 8/111 |
| 3,864,271 | 2/1975 | Stalter | 252/99 |
| 4,320,102 | 3/1982 | Dalton et al. | 423/273 |
| 5,565,190 | 10/1996 | Santalucia et al. | 424/53 |
| 5,599,525 | 2/1997 | Hsu et al. | 424/53 |
| 5,599,527 | 2/1997 | Hsu et al. | 424/53 |
| 5,614,174 | 3/1997 | Hsu et al. | 424/53 |
| 5,648,064 | 7/1997 | Gaffar et al. | 424/53 |
| 5,683,680 | 11/1997 | Santalucia et al. | 424/53 |
| 5,690,913 | 11/1997 | Hsu et al. | 424/53 |
| 5,698,182 | 12/1997 | Prencipe et al. | 424/53 |

*Primary Examiner*—Shep K. Rose
*Attorney, Agent, or Firm*—Paul Shapiro

[57] ABSTRACT

An aqueous abrasive whitening composition containing a peroxide whitening compound which is chemically and physically stable and exhibits heightened and rapid whitening of teeth and stain removal which comprises a combination of water, calcined alumina abrasive and a peroxide compound.

14 Claims, No Drawings

STABLE AQUEOUS ABRASIVE PEROXIDE TOOTH WHITENING DENTIFRICE

This application is a continuation-in-part of copending application Ser. No. 08/692,841 filed Aug. 2, 1996.

BACKGROUND OF THE INVENTION

1. Field of the Invention

This invention relates generally to peroxide containing preparations for whitening human teeth, and more particularly, to a stable peroxide dentifrice composition which when applied onto the surface of teeth acts to both whiten and remove stain from teeth.

2. The Prior Art

A tooth is comprised of an inner dentin layer and an outer hard enamel layer that is the protective layer of the tooth. The enamel layer of a tooth is naturally an opaque white or slightly off-white color. It is this enamel layer that can become stained or discolored. The enamel layer of a tooth is composed of hydroxyapatite mineral crystals that create a somewhat porous surface. It is believed that this porous nature of the enamel layer is what allows staining agents and discoloring substances to permeate the enamel and discolor the tooth.

Many substances that a person confronts or comes in contact with on a daily basis can "stain" or reduce the "whiteness" of one's teeth. In particular, the foods, tobacco products and fluids such as tea and coffee that one consumes tend to stain one's teeth. These products or substances tend to accumulate on the enamel layer of the tooth and form a film over the teeth. These staining and discoloring substances can then permeate the enamel layer. This problem occurs gradually over many years, but imparts a noticeable discoloration of the enamel of one's teeth.

There are available in the marketplace non-abrasive gel compositions for home use which contain 1–3% by weight concentrations of hydrogen peroxide or urea peroxide and when brushed on the teeth effect whitening and removal of stains.

A drawback to the use of these peroxide based whitening gels is the tendency of the peroxide component to decompose within a relatively short period of time following manufacture with concomitant loss of all or a substantial amount of the available oxygen thereby limiting the efficacy of these products as teeth whitening compositions. Peroxy compounds such as hydrogen peroxide are notoriously unstable with respect to maintenance of peroxide level and have been found to be difficult to formulate into aqueous gels or pastes which will have an adequate shelf-life and yet will readily liberate oxygen when applied to teeth. Therefore, the prior art, for example U.S. Pat. No. 4,988,450 and U.S. Pat. No. 3,657,413, in formulating oxygen liberating compositions for the whitening of teeth, utilize anhydrous powders or water-free pastes or gels which must be protected against chemical interaction. A drawback to the use of such anhydrous products is that, due to the absence of water, application of the product tends to desiccate oral tissue which leads to irritation and tissue damage. Further, due to the absence of water in the formulation of the anhydrous product, the product exhibits poor, often unacceptable rheological properties due to inadequate hydration of the gelling agents added to thicken the product.

Dentifrice whitening products formulated with peroxy compounds normally do not contain abrasive polishing agents as such materials activate the rapid decomposition of the peroxy compounds whereby the oxygen whitening agent is prematurely released. The gas evolution is especially undesirable as such gas evolution can cause swelling and/or bursting of tubes containing the dentifrice product. Capped tubes filled with dentifrice products containing peroxide compounds and silica abrasives have been known to explode within one day after filling. U.S. Pat. No. 5,256,402 discloses that when alumina abrasives are substituted for silica, the filled product is pocketed with gas bubbles within days of filling.

A drawback to the use of whitening products which are formulated without abrasives is that, in addition to the stability problem, the products are not effective in stain removal. Thus the abrasive or polishing agent incorporated in a dentifrice acts to debride and physically scrub the external surface of teeth. This scrubbing action removes filmy bacterial and plaque layers as well as some of the stains and discoloring pigments that are found on teeth that cause the undesired discoloration. These abrasive agents also microabrade the tooth so as to polish the teeth to give the enamel a more lustrous appearance and a higher optical sheen. This micro abrasion action enhances the scrubbed teeth's ability to reflect white light and thereby appear brighter.

The aqueous abrasive toothpaste composition disclosed in U.S. Pat. No. 5,256,402 contains a urea or hydrogen peroxide compound an alkali pyrophosphate salt and a calcium pyrophosphate abrasive which is stable with respect to active oxygen level. A drawback to the abrasive peroxide oral composition disclosed in U.S. Pat. No. 5,256,402 is that although the peroxide compound is stable, additional stability is required when the product is subjected to extended storage periods at abnormally high temperatures.

In copending patent application Ser. No. 08/692,841 filed Aug. 2, 1996 there is disclosed an aqueous abrasive provide dentifrice composition which is physically and chemically stable and effects rapid whitening of teeth and stain removal which contains a dicalcium phosphate abrasive, a peroxide compound, a humectant containing a polyethylene glycol, a metal ion complexing agent, an antioxidant compound and a polyoxyethylene-polyoxypropylene block copolymer gelling agent, the pH of the dentifrice being buffered in the range of about 5.8 to about 7.2.

Although the aqueous abrasive peroxide dentifrice composition of copending application Ser. No. 08/692,841 is effective in whitening teeth, the art continuously seeks dentifrice compositions of greater whitening efficacy and stability.

SUMMARY OF THE INVENTION

In accordance with the present invention, it has now been found that an aqueous abrasive peroxide dentifrice composition which is physically and chemically stable and effects rapid whitening of teeth and stain removal is obtained using a calcined alumina abrasive, a peroxide compound, and a stabilizer compound.

The stability of the dentifrice composition of the present invention is unexpected, for as previously discussed, the prior art (U.S. Pat. No. 5,256,402) understood that dentifrices containing peroxy compounds and alumina abrasives have poor stability.

DESCRIPTION OF THE PREFERRED EMBODIMENTS

It is critical to the practice of the present invention that the form of alumina used as the abrasive in the dentifrice compositions of the present invention be calcined alumina, a form of alumina produced by calcination of aluminum hydroxide into alpha-$Al_2O_3$ which is thermodynamically stable at temperatures above 1200° C. Calcined alumina abrasives are available commercially. A preferred calcined alumina abrasive is sold by Alcan Chemicals under the designation Baco Aluminum Oxide.

The calcined alumina abrasive is incorporated in the whitening composition of the present invention at a concentration of about 1 to 30% by weight and preferably about 5 to about 10% by weight.

The peroxide component of the composition of the invention is included in an amount sufficient to allow release of sufficient oxygen during brushing of teeth to effect whitening thereof. Typically, the peroxide compound can be employed in the composition of the present invention in amounts so that at least about 0.5% of the composition comprises a peroxide. Preferably, the peroxide comprises from about 0.5 to about 10% by weight of the composition. More preferably, the peroxide comprises from about 0.75 to about 5% by weight of the composition. Examples of suitable peroxide compounds used to prepare the compositions of the present invention include metal peroxides such as calcium peroxide, hydrogen peroxide and organic peroxides including urea peroxide, glyceryl peroxide, benzoyl peroxide and the like. A preferred peroxide compound is hydrogen peroxide.

The peroxide and calcined alumina abrasive used to prepare the whitening composition of the present invention are dissolved or suspended in a vehicle comprised of water and a humectant such as a polyethylene glycol and glycerin. Water constitutes about 7 to about 40% by weight of the whitening composition of the present invention and preferably about 20 to about 30% by weight.

Illustrative of polyethylene glycols useful in the practice of the present invention include polyethylene glycols known by the trademark Carbowax which are nonionic polymers of ethylene oxide having the general formula: $HOCH_2(CH_2OCH_2)_nCH_2OH$ wherein n represents the average number of oxyethylene groups. The Carbowax polyethylene glycols are designated by a number such as 400, 600, 800, 1000, 2000 which represents the average molecular weight. The molecular weight range of the polyethylene glycols used herein is about 200 to about 2000 and preferably about 600 hereinafter referred to as PEG 600.

The polyethylene glycol component included in the composition of the present invention constitutes about 10 to about 30% by weight of the whitening composition and preferably about 15 to about 20% by weight.

Glycerin may be included in the whitening composition of the present invention in the range from 0 to about 10% by weight of the whitening composition. Concentrations of glycerin substantially in excess of 10% by weight have been found to cause physical destabilization (liquefaction) of the composition and therefore such excess should be avoided.

Gelling agents are included in the abrasive peroxide compositions of the present invention in amounts from about 10% to about 25% by weight of the composition and preferably about 12 to about 20% by weight. Examples of suitable gelling agents include polyoxyethylene polyoxypropylene block copolymers having the formula $HO(C_2H_4O)_b(C_3H_6O)_a(C_2H_4O)_bH$ wherein a is an integer such that the hydrophobic base represented by $(C_3H_6O)$ has a molecular weight of about 2750 to 4000, b is an integer such that the hydrophilic portion represented by $(C_2H_4O)$ constitutes about 70–80% by weight of the copolymer. Block copolymers of this composition are available commercially under the trademark Pluronic F type.

Pluronic F127, which has a molecular weight of range of about 9000 to about 14000 and contains 70% of the hydrophilic polyoxyethylene moiety is preferred for use as a gelling agent in the practice of the present invention.

Other examples of gelling agents which may be employed are the well-known carboxy vinyl polymers of extremely high molecular weight sold under the trade name Carbopol by the B.F. Goodrich Chemical Company as well as carboxypolymethylene polymers which comprise a major portion of one or more alpha, beta-olinfinically unsaturated carboxylic acids, and a minor portion of a polyalkenyl polyether or a polyol, i.e., a copolymer or acrylic acid cross-linked with from about 0.75% to 1.5% of polyally sucrose.

The presence of metal ion chelating agents and antioxidants (oxygen scavengers) stabilizer compounds in the dentifrice compositions of the present invention contribute to the chemical stability of the abrasive peroxide composition. Examples of suitable metal ion chelating agents include alkali metal stannates such as sodium and potassium stannate, ethylenediaminetetracetic acid and its salts. Examples of antioxidants useful in the practice of the present invention include butylated hydroxy toluene (BHT), nordihydroguaiaretic acid, propyl gallate and trihydroxybutyrophenone. The metal ion chelating agents are incorporated in the compositions of the present invention at a concentration of about 0.01 to about 1% by weight and the antioxidant is incorporated at a concentration of about 0.05 to about 0.20% by weight and preferably about 0.02 to about 0.05% by weight.

In preparing the abrasive peroxide compositions of the present invention, the pH of the composition is adjusted to a range between about 3.0 and about 8 and preferably about between about 5 and about 7.

Pyrophosphate salts having anti-tartar efficacy such as dialkali or tetra-alkali metal pyrophosphate salts such as $Na_4P_2O_7$ (TSPP), $K_4P_2O_7$, $Na_2K_2P_2O_7$, $Na_2H_2P_2O_7$ (SAPP), and $K_2H_2P_2O_7$, may be included in the composition of the present invention at a concentration of about 0.5 to about 8.0% by weight and preferably about 1.5 to 3.5% by weight. In addition to their antitartar efficacy, pyrophosphate salts serve a dual function as supplementary metal ion complexing agents.

Fluoride salts having anti-caries efficacy may also be incorporated in the dentifrice of the present invention and are characterized by their ability to release fluoride ions in water, for example, sodium fluoride, potassium fluoride, sodium fluorosilicate, ammonium fluorosilicate and sodium monofluorophosphate (NaMFP). It is preferable to employ a fluoride salt to release about 10–1500 ppm of fluoride ion.

A surfactant is also included in the whitening composition of the present invention and serves as a solubilizing, dispersing, emulsifying and wetting agent and is especially effective in solubilizing the flavor ingredient present. Surfactants which may be used in the practice of the present invention include cationic surfactants, anionic surfactants such as sodium laurylsulfate and sodium laurylsulfoacetate, ampholytic and amphoteric surfactants like cocoamidopropyl betaine.

The flavor ingredient constitutes about 0.5–5.0% by weight of the dentifrice composition of the present invention. Suitable flavoring constituents are flavoring oils, e.g., oils of spearmint, peppermint, wintergreen, menthol, cineole, limonene, menthone and menthyl acetate.

A sweetening material is preferably also employed as a complement to the flavoring material. Suitable sweetening agents are water soluble and include sodium saccharin, sodium cyclamate, xylitol, aspartame and the like, in concentrations of about 0.01 to 1.0% by weight. Sodium saccharin is preferred.

To prepare the whitening compositions of the present invention, water soluble salts such as sodium saccharin and sodium monoflurophosphate (NaMFP) are dissolved in an aqueous vehicle containing a humectant such as PEG 600 and glycerin. The vehicle is heated to a temperature of about 130°–170° C., followed by the addition of a polyoxyethylene-polyoxypropylene block copolymer gelling agent and the ingredients are mixed until a gel phase is formed. An abrasive compound such as calcium pyrophosphate is added to the gel and mixed to form a paste. The paste when formed is cooled to about 90°–130° F., preferably about 100° F. A metal ion chelating agent, antioxidant, buffering agent and peroxide compound are then added to the paste and the ingredients mixed to obtain an homogenous mixture. The flavor and surfactant, are then added to the mixture to obtain a finished tooth whitening paste of the present invention.

It has been determined that when pyrophosphate salts are used in the manufacture of the whitening compositions of the present invention, attempts to dissolve such salts in the aqueous vehicle at temperatures in excess of 130° F. should be avoided as such temperature conditions bring into solution levels of pyrophosphate salt in excess of the solubility capacity of the salt thereby creating a supersaturated condition with respect to the excess salt. During storage at lower, ambient temperatures, the excess pyrophosphate salt crystallizes out from the whitening composition matrix forming insoluble solid matter which is cosmetically unacceptable and may have the further disadvantage of promoting chemical instability.

It is therefore preferred in the practice of the present invention, that when pyrophosphate salts are to be included in the whitening formulation that during the manufacture of the whitening composition any pyrophosphate salt added to the composition is premixed in the humectant and the premixture added to the composition matrix at a temperature no higher than 100° F.

The following example further illustrates the present invention, but it is understood that the invention is not limited thereto. All amounts and proportions referred to herein and in the appended claims are by weight unless otherwise indicated.

EXAMPLE I

A whitening abrasive peroxide of the present invention containing calcined alumina designated "Composition A" was prepared. For purposes of comparison, a comparative whitening peroxide dentifrice (Composition B) was prepared in the same manner as Composition A except calcined alumina was not present as an abrasive. The ingredients of Compositions A and B are recorded in Table I below.

TABLE I

COMPOSITIONS A–B

| Ingredients | Composition A (Weight %) | Composition B (Weight %) |
| --- | --- | --- |
| Water | 24.28 | 25.64 |
| PEG 600 | 17.42 | 17.42 |
| Glycerin | 7.42 | 7.42 |
| TSPP | 2.00 | 2.00 |
| Pluronic F-127 | 15.00 | 15.00 |
| Calcined Alumina | 10 | 0 |
| Calcium Pyrophosphate | 15.00 | 25.00 |
| Na MFP | 0.76 | 0.76 |
| Saccharin | 0.50 | 0.50 |
| Phosphoric Acid | 1.000 | 0.50 |
| H2O2 (35%) containing sodium stannate | 4.29 | 3.43 |
| Flavor | 1.50 | 1.50 |
| BHT | 0.03 | 0.03 |
| SLS | 0.80 | 0.8 |
| pH | 7.02 | 6.70 |

Compositions A and B were prepared by dispersing TSPP in a mixture of PEG 600 and glycerin and heating to 130° F. while stirring. Water was added to the mixture and the ingredients mixed for about 5 minutes Saccharin and sodium monofluorophosphate (Na MFP) were added and the resultant mixture stirred for 10 minutes, followed by the addition of Pluronic F127 and stirring at 130° F., for 20 minutes. The mixture was then deaerated for 5 minutes and calcium pyrophosphate was added and the resulting paste mixed for 15 minutes at high speed under vacuum. Potassium stannate premixed with $H_2O_2$ was added to the paste which was further mixed for 10 minutes under vacuum at high speed. BHT premixed with flavor oil was then added to the paste and mixed under vacuum for 5 minutes. Sodium lauryl sulfate (SLS) was then added under vacuum for 5 minutes at low speed. When necessary, phosphoric acid was added to adjust the pH of the composition to the desired level.

The chemical stability of Compositions A and B was determined by initially analyzing the compositions for active oxygen (AO) and then storing the composition for a 6 week period at elevated temperatures 105° F., 120° F. and again analyzing the dentifrice for AO.

The results of these analyses are summarized in Table II below.

TABLE II

Composition Stability

| Composition | AO % Initial 105° F. | AO % Initial 120° F. | AO % 6 weeks @ 105° F. | AO % 6 weeks @ 120° F. | AO % Recovery 105° F. | AO % Recovery 120° F. |
| --- | --- | --- | --- | --- | --- | --- |
| A | 1.49 | 1.49 | 1.40 | 1.31 | 94.0 | 87.9 |
| B | 1.19 | 1.19 | 1.06 | 1.01 | 89.0 | 84.9 |

The data recorded in Table II indicate that the stability of the peroxide dentifrices of the present invention (Composition A) containing a calcined alumina abrasive is 94% after 6 weeks at 105° F. and greater than 87% after 6 weeks at 120° F. indicating that the dentifrice composition is relatively stable and even has a higher stability than a similar dentifrice (Composition B) in which calcined alumina is absent.

To test the whitening efficacy of Composition A, bovine teeth were stained by intermittent exposure of the bovine teeth to a staining broth containing finely ground instant coffee, instant tea, gastric mucin, trypticase, soy broth, and Sarcina lutea turtox (a chromogenic migroorganism) throughout a four day period. Stained bovine teeth specimens selected for the test showed the same amount of discoloration. The selected specimens were then brushed with a 1:1 toothpaste/water slurry for 200 brush strokes. Whitening efficacy was determined by the increase in L value measured by a Minolta chronometer before and after brushing. L is a measure of response to the eye to lightness and darkness. A change in L (ΔL) is then calculated. The higher the ΔL value, the whiter teeth appear.

For purposes of comparison, the whitening evaluation procedure of the Example was repeated with the exception that Composition B was substituted for Composition A.

The results of the brushing study using the stained bovine teeth specimens are shown in Table III.

TABLE III

| Composition | ΔL (±std. deviation) |
|---|---|
| A | 17.2 ± 3.9 |
| B | 11.3 ± 4.5 |

The data in Table III indicate that the dentifrice of the present invention (Composition A) containing calcined alumina is substantially (52%) more effective in removing stain from teeth than comparative Composition B, which did not contain calcined alumina, the results being statistically significant at the 95% level of confidence.

What is claimed is:

1. An aqueous tooth whitening composition which is chemically stable and effects whitening and stain removal from teeth which comprises a vehicle containing water, a humectant, a calcined alumina abrasive, hydrogen peroxide, and about 0.05 to about 0.2% by weight of an antioxidant and about 0.1 to about 1% by weight of metal ion chelating agent.

2. The composition of claim 1 wherein the peroxide compound is present in the composition at a concentration of about 0.5 to about 10% by weight of the composition.

3. The composition of claim 1 wherein the calcined alumina is present in the composition at a concentration of about 1 to about 30% by weight of the composition.

4. The composition of claim 1 wherein the water is present in the composition at a concentration of about 7 to about 40% by weight.

5. A method for whitening teeth which comprises preparing an aqueous tooth whitening composition containing a calcined alumina abrasive hydrogen peroxide and about 0.05 to about 0.2% by weight of an antioxidant and about 0.1 to about 1% by weight of a metal chelating agent, which composition is chemically and physically stable and then applying the composition to stained teeth to effect whitening of and stain removal from teeth.

6. The method of claim 5 wherein the peroxide compound is present in the admixture at a concentration of about 0.5 to about 10% by weight of the composition.

7. The method of claim 5 wherein the calcined alumina abrasive compound is present in the composition at a concentration of about 1 to about 30% by weight.

8. The method of claim 5 wherein water is present in the composition at a concentration of about 7 to about 40% by weight.

9. The composition of claim 1 wherein the metal chelating agent is an alkali metal stannate.

10. The composition of claim 9 wherein the alkali metal stannate is sodium stannate.

11. The composition of claim 1 wherein the antioxidant is butylated hydroxy toluene.

12. The method of claim 5 wherein the metal chelating agent is an alkali metal stannate.

13. The method of claim 12 wherein the alkali metal stannate is sodium stannate.

14. The method of claim 5 wherein the antioxidant is butylated hydroxy toluene.

* * * * *